(12) United States Patent
Marczyk et al.

(10) Patent No.: US 8,342,378 B2
(45) Date of Patent: Jan. 1, 2013

(54) ONE HANDED STAPLER

(75) Inventors: Stanislaw Marczyk, Stratford, CT (US);
Russell Pribanic, New Milford, CT
(US); Adam J. Ross, Prospect, CT (US);
Michael A. Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 304 days.

(21) Appl. No.: 12/792,244

(22) Filed: Jun. 2, 2010

(65) Prior Publication Data
US 2011/0036892 A1 Feb. 17, 2011

Related U.S. Application Data

(60) Provisional application No. 61/234,369, filed on Aug. 17, 2009.

(51) Int. Cl.
*A61B 17/068* (2006.01)
(52) U.S. Cl. ...................... 227/176.1; 227/19
(58) Field of Classification Search ............... 227/176.1, 227/19
See application file for complete search history.

(56) References Cited

U.S. PATENT DOCUMENTS

| | | | |
|---|---|---|---|
| 3,079,606 A | 3/1963 | Bobrov et al. |
| 3,490,675 A | 1/1970 | Green et al. |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |

(Continued)

FOREIGN PATENT DOCUMENTS

AU 5476586 9/1986

(Continued)

OTHER PUBLICATIONS

European Search Report for corresponding EP 10 25 1449 application, date of completion is Oct. 25, 2010 (3 pages).

(Continued)

*Primary Examiner* — Brian D Nash

(57) ABSTRACT

The present disclosure is directed to a surgical instrument, which includes a handle assembly and an elongate member having two jaw members. The second jaw member is movable in relation to the first jaw member between an open position and a closed position. The first jaw member is supported by the elongate body and contains a plurality of fasteners. The elongate member extends distally from the handle assembly and defines both a longitudinal axis and a distal portion. A switch is placed about the handle assembly to allow the handle assembly to operate in multiple modes.

18 Claims, 4 Drawing Sheets

U.S. PATENT DOCUMENTS

| | | |
|---|---|---|
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | deSalis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,300,081 A * | 4/1994 | Young et al. ............. 606/143 |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |

| Patent | Date | Inventor |
|---|---|---|
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,732,871 A | 3/1998 | Clark et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Ratcliff et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |

| | | | | | | |
|---|---|---|---|---|---|---|
| 6,991,627 B2 | 1/2006 | Madhani et al. | | 7,467,740 B2 | 12/2008 | Shelton, IV et al. |
| 6,994,714 B2 | 2/2006 | Vargas et al. | | 7,472,814 B2 | 1/2009 | Mastri et al. |
| 7,000,818 B2 | 2/2006 | Shelton, IV et al. | | 7,472,815 B2 | 1/2009 | Shelton, IV et al. |
| 7,000,819 B2 | 2/2006 | Swayze et al. | | 7,472,816 B2 | 1/2009 | Holsten et al. |
| 7,032,799 B2 | 4/2006 | Viola et al. | | 7,473,258 B2 | 1/2009 | Clauson et al. |
| 7,044,352 B2 | 5/2006 | Shelton, IV et al. | | 7,481,347 B2 | 1/2009 | Roy |
| 7,044,353 B2 | 5/2006 | Mastri et al. | | 7,481,348 B2 | 1/2009 | Marczyk |
| 7,055,730 B2 | 6/2006 | Ehrenfels et al. | | 7,481,349 B2 | 1/2009 | Holsten et al. |
| 7,055,731 B2 | 6/2006 | Shelton, IV et al. | | 7,487,899 B2 | 2/2009 | Shelton, IV et al. |
| 7,059,508 B2 | 6/2006 | Shelton, IV et al. | | 7,490,749 B2 | 2/2009 | Schall et al. |
| 7,070,083 B2 | 7/2006 | Jankowski | | 7,494,039 B2 | 2/2009 | Racenet et al. |
| 7,083,075 B2 | 8/2006 | Swayze et al. | | 7,500,979 B2 | 3/2009 | Hueil et al. |
| 7,097,089 B2 | 8/2006 | Marczyk | | 7,503,474 B2 | 3/2009 | Hillstead et al. |
| 7,111,769 B2 | 9/2006 | Wales et al. | | 7,506,790 B2 | 3/2009 | Shelton, IV |
| 7,114,642 B2 | 10/2006 | Whitman | | 7,510,107 B2 | 3/2009 | Timm et al. |
| 7,121,446 B2 | 10/2006 | Arad et al. | | 7,513,408 B2 | 4/2009 | Shelton, IV et al. |
| 7,128,253 B2 | 10/2006 | Mastri et al. | | 7,517,356 B2 | 4/2009 | Heinrich |
| 7,128,254 B2 | 10/2006 | Shelton, IV et al. | | 7,537,602 B2 | 5/2009 | Whitman |
| 7,140,527 B2 | 11/2006 | Ehrenfels et al. | | 7,543,729 B2 | 6/2009 | Ivanko |
| 7,140,528 B2 | 11/2006 | Shelton, IV | | 7,543,730 B1 | 6/2009 | Marczyk |
| 7,143,923 B2 | 12/2006 | Shelton, IV et al. | | 7,543,731 B2 | 6/2009 | Green et al. |
| 7,143,924 B2 | 12/2006 | Scirica et al. | | 7,556,185 B2 | 7/2009 | Viola |
| 7,143,925 B2 | 12/2006 | Shelton, IV et al. | | 7,556,186 B2 | 7/2009 | Milliman |
| 7,143,926 B2 | 12/2006 | Shelton, IV et al. | | 7,559,450 B2 | 7/2009 | Wales et al. |
| 7,147,138 B2 | 12/2006 | Shelton, IV | | 7,559,452 B2 | 7/2009 | Wales et al. |
| 7,159,750 B2 | 1/2007 | Racenet et al. | | 7,559,453 B2 | 7/2009 | Heinrich et al. |
| 7,172,104 B2 | 2/2007 | Scirica et al. | | 7,559,937 B2 | 7/2009 | de la Torre et al. |
| 7,188,758 B2 | 3/2007 | Viola et al. | | 7,565,993 B2 | 7/2009 | Milliman et al. |
| 7,207,471 B2 | 4/2007 | Heinrich et al. | | 7,568,603 B2 | 8/2009 | Shelton, IV et al. |
| 7,213,736 B2 | 5/2007 | Wales et al. | | 7,568,604 B2 | 8/2009 | Ehrenfels et al. |
| 7,225,963 B2 | 6/2007 | Scirica | | 7,571,845 B2 | 8/2009 | Viola |
| 7,225,964 B2 | 6/2007 | Mastri et al. | | 7,575,144 B2 | 8/2009 | Ortiz et al. |
| 7,238,195 B2 | 7/2007 | Viola | | 7,584,880 B2 | 9/2009 | Racenet et al. |
| 7,246,734 B2 | 7/2007 | Shelton, IV | | 7,588,175 B2 | 9/2009 | Timm et al. |
| 7,258,262 B2 | 8/2007 | Mastri et al. | | 7,588,176 B2 | 9/2009 | Timm et al. |
| 7,278,562 B2 | 10/2007 | Mastri et al. | | 7,588,177 B2 | 9/2009 | Racenet |
| 7,278,563 B1 | 10/2007 | Green | | 7,597,229 B2 | 10/2009 | Boudreaux et al. |
| 7,287,682 B1 | 10/2007 | Ezzat et al. | | 7,597,230 B2 | 10/2009 | Racenet et al. |
| 7,293,685 B2 | 11/2007 | Ehrenfels et al. | | 7,604,150 B2 | 10/2009 | Boudreaux |
| 7,296,724 B2 | 11/2007 | Green et al. | | 7,604,151 B2 | 10/2009 | Hess et al. |
| 7,296,772 B2 | 11/2007 | Wang | | 7,607,557 B2 | 10/2009 | Shelton, IV et al. |
| 7,300,444 B1 | 11/2007 | Nielsen et al. | | 7,611,038 B2 | 11/2009 | Racenet et al. |
| 7,303,108 B2 | 12/2007 | Shelton, IV | | 7,617,961 B2 | 11/2009 | Viola |
| 7,308,998 B2 | 12/2007 | Mastri et al. | | 7,624,902 B2 | 12/2009 | Marczyk et al. |
| 7,328,828 B2 | 2/2008 | Ortiz et al. | | 7,624,903 B2 | 12/2009 | Green et al. |
| 7,328,829 B2 | 2/2008 | Arad et al. | | 7,631,793 B2 | 12/2009 | Rethy et al. |
| 7,354,447 B2 | 4/2008 | Shelton, IV et al. | | 7,631,794 B2 | 12/2009 | Rethy et al. |
| 7,357,287 B2 | 4/2008 | Shelton, IV et al. | | 7,635,073 B2 | 12/2009 | Heinrich |
| 7,364,061 B2 | 4/2008 | Swayze et al. | | 7,635,074 B2 | 12/2009 | Olson et al. |
| 7,367,485 B2 | 5/2008 | Shelton, IV et al. | | 7,635,373 B2 | 12/2009 | Ortiz |
| 7,380,695 B2 | 6/2008 | Doll et al. | | 7,637,409 B2 | 12/2009 | Marczyk |
| 7,380,696 B2 | 6/2008 | Shelton, IV et al. | | 7,637,410 B2 | 12/2009 | Marczyk |
| 7,399,310 B2 | 7/2008 | Edoga et al. | | 7,641,091 B2 | 1/2010 | Olson et al. |
| 7,401,720 B1 | 7/2008 | Durrani | | 7,641,093 B2 | 1/2010 | Doll et al. |
| 7,404,508 B2 | 7/2008 | Smith et al. | | 7,641,095 B2 | 1/2010 | Viola |
| 7,404,509 B2 | 7/2008 | Ortiz et al. | | 7,644,848 B2 | 1/2010 | Swayze et al. |
| 7,407,074 B2 | 8/2008 | Ortiz et al. | | 7,648,055 B2 | 1/2010 | Marczyk |
| 7,407,077 B2 | 8/2008 | Ortiz et al. | | 7,651,017 B2 | 1/2010 | Ortiz et al. |
| 7,407,078 B2 | 8/2008 | Shelton, IV et al. | | 7,654,431 B2 | 2/2010 | Hueil et al. |
| 7,416,101 B2 | 8/2008 | Shelton, IV et al. | | 7,658,311 B2 | 2/2010 | Boudreaux |
| 7,419,080 B2 | 9/2008 | Smith et al. | | 7,658,312 B2 | 2/2010 | Vidal et al. |
| 7,419,495 B2 | 9/2008 | Menn et al. | | 7,665,646 B2 | 2/2010 | Prommersberger |
| 7,422,139 B2 | 9/2008 | Shelton, IV et al. | | 7,665,647 B2 | 2/2010 | Shelton, IV et al. |
| 7,431,189 B2 | 10/2008 | Shelton, IV et al. | | 7,669,746 B2 | 3/2010 | Shelton, IV |
| 7,434,715 B2 | 10/2008 | Shelton, IV et al. | | 7,670,334 B2 | 3/2010 | Hueil et al. |
| 7,434,717 B2 | 10/2008 | Shelton, IV et al. | | 7,673,780 B2 | 3/2010 | Shelton, IV et al. |
| 7,438,208 B2 | 10/2008 | Larson | | 7,673,781 B2 | 3/2010 | Swayze et al. |
| 7,438,209 B1 | 10/2008 | Hess et al. | | 7,673,782 B2 | 3/2010 | Hess et al. |
| 7,441,684 B2 | 10/2008 | Shelton, IV et al. | | 7,673,783 B2 | 3/2010 | Morgan et al. |
| 7,441,685 B1 | 10/2008 | Boudreaux | | 7,678,121 B1 | 3/2010 | Knodel |
| 7,448,525 B2 | 11/2008 | Shelton, IV et al. | | 7,681,772 B2 | 3/2010 | Green et al. |
| 7,451,904 B2 | 11/2008 | Shelton, IV | | 7,682,367 B2 | 3/2010 | Shah et al. |
| 7,455,208 B2 | 11/2008 | Wales et al. | | 7,682,368 B1 | 3/2010 | Bombard et al. |
| 7,458,494 B2 | 12/2008 | Matsutani et al. | | 7,690,547 B2 | 4/2010 | Racenet et al. |
| 7,461,767 B2 | 12/2008 | Viola et al. | | 7,694,865 B2 | 4/2010 | Scirica |
| 7,462,185 B1 | 12/2008 | Knodel | | 2004/0007608 A1 | 1/2004 | Ehrenfels et al. |
| 7,464,846 B2 | 12/2008 | Shelton, IV et al. | | 2004/0050902 A1 | 3/2004 | Green |
| 7,464,848 B2 | 12/2008 | Green et al. | | 2004/0093029 A1 | 5/2004 | Zubik et al. |
| 7,464,849 B2 | 12/2008 | Shelton, IV et al. | | 2004/0094597 A1 | 5/2004 | Whitman |

| Pub. No. | Date | Name |
|---|---|---|
| 2004/0108357 A1 | 6/2004 | Milliman |
| 2004/0149802 A1 | 8/2004 | Whitman |
| 2004/0173659 A1 | 9/2004 | Green |
| 2004/0199180 A1 | 10/2004 | Knodel et al. |
| 2004/0199181 A1 | 10/2004 | Knodel et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2004/0267311 A1 | 12/2004 | Viola et al. |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |
| 2005/0023324 A1 | 2/2005 | Doll et al. |
| 2005/0023325 A1 | 2/2005 | Gresham |
| 2005/0067457 A1 | 3/2005 | Shelton |
| 2005/0067458 A1 | 3/2005 | Swayze et al. |
| 2005/0067459 A1 | 3/2005 | Swayze et al. |
| 2005/0067460 A1 | 3/2005 | Milliman |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0082336 A1 | 4/2005 | Ivanko |
| 2005/0103819 A1 | 5/2005 | Racenet |
| 2005/0119669 A1 | 6/2005 | Demmy |
| 2005/0127131 A1 | 6/2005 | Mastri |
| 2005/0145671 A1 | 7/2005 | Viola |
| 2005/0159778 A1 | 7/2005 | Heinrich et al. |
| 2005/0165415 A1 | 7/2005 | Wales |
| 2005/0173490 A1 | 8/2005 | Shelton, IV |
| 2005/0178813 A1 | 8/2005 | Swayze et al. |
| 2005/0184121 A1 | 8/2005 | Heinrich |
| 2005/0184123 A1 | 8/2005 | Scirica et al. |
| 2005/0184124 A1 | 8/2005 | Scirica et al. |
| 2005/0184125 A1 | 8/2005 | Marczyk |
| 2005/0184126 A1 | 8/2005 | Green et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0230453 A1 | 10/2005 | Viola |
| 2005/0263562 A1 | 12/2005 | Shelton, IV et al. |
| 2005/0279804 A1 | 12/2005 | Scirica et al. |
| 2006/0000867 A1 | 1/2006 | Shelton, IV et al. |
| 2006/0000868 A1 | 1/2006 | Shelton, IV et al. |
| 2006/0011699 A1 | 1/2006 | Olson et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0043147 A1 | 3/2006 | Mastri et al. |
| 2006/0049229 A1 | 3/2006 | Milliman et al. |
| 2006/0049230 A1 | 3/2006 | Shelton, IV et al. |
| 2006/0060630 A1 | 3/2006 | Shelton, IV et al. |
| 2006/0081678 A1 | 4/2006 | Ehrenfels et al. |
| 2006/0097026 A1 | 5/2006 | Shelton, IV |
| 2006/0124688 A1 | 6/2006 | Racenet et al. |
| 2006/0124689 A1 | 6/2006 | Arad et al. |
| 2006/0138193 A1 | 6/2006 | Viola et al. |
| 2006/0138194 A1 | 6/2006 | Viola et al. |
| 2006/0151567 A1 | 7/2006 | Roy |
| 2006/0151568 A1 | 7/2006 | Weller et al. |
| 2006/0151569 A1 | 7/2006 | Ehrenfels et al. |
| 2006/0175375 A1 | 8/2006 | Shelton, IV et al. |
| 2006/0180634 A1 | 8/2006 | Shelton, IV et al. |
| 2006/0201990 A1 | 9/2006 | Mastri et al. |
| 2006/0201991 A1 | 9/2006 | Mastri et al. |
| 2006/0226195 A1 | 10/2006 | Scirica et al. |
| 2006/0226196 A1 | 10/2006 | Hueil et al. |
| 2006/0255090 A1 | 11/2006 | Milliman et al. |
| 2006/0278680 A1 | 12/2006 | Viola et al. |
| 2006/0278681 A1 | 12/2006 | Viola et al. |
| 2006/0289600 A1 | 12/2006 | Wales et al. |
| 2006/0289602 A1 | 12/2006 | Wales et al. |
| 2007/0023477 A1 | 2/2007 | Whitman et al. |
| 2007/0027469 A1 | 2/2007 | Smith et al. |
| 2007/0034669 A1 | 2/2007 | de la Torre et al. |
| 2007/0034670 A1 | 2/2007 | Racenet et al. |
| 2007/0045379 A1 | 3/2007 | Shelton, IV |
| 2007/0045380 A1 | 3/2007 | Mastri et al. |
| 2007/0068989 A1 | 3/2007 | Shelton, IV |
| 2007/0068990 A1 | 3/2007 | Shelton, IV et al. |
| 2007/0073340 A1 | 3/2007 | Shelton, IV et al. |
| 2007/0073341 A1 | 3/2007 | Smith et al. |
| 2007/0075114 A1 | 4/2007 | Shelton, IV et al. |
| 2007/0075115 A1 | 4/2007 | Olson et al. |
| 2007/0075116 A1 | 4/2007 | Whitman |
| 2007/0083233 A1 | 4/2007 | Ortiz et al. |
| 2007/0083234 A1 | 4/2007 | Shelton, IV et al. |
| 2007/0084896 A1 | 4/2007 | Doll et al. |
| 2007/0084897 A1 | 4/2007 | Shelton, IV et al. |
| 2007/0084898 A1 | 4/2007 | Scirica |
| 2007/0084899 A1 | 4/2007 | Taylor |
| 2007/0102472 A1 | 5/2007 | Shelton, IV |
| 2007/0102473 A1 | 5/2007 | Shelton, IV |
| 2007/0102474 A1 | 5/2007 | Shelton, IV |
| 2007/0102475 A1 | 5/2007 | Ortiz et al. |
| 2007/0102476 A1 | 5/2007 | Shelton, IV |
| 2007/0106317 A1 | 5/2007 | Shelton, IV |
| 2007/0108252 A1 | 5/2007 | Racenet et al. |
| 2007/0114261 A1 | 5/2007 | Ortiz et al. |
| 2007/0114262 A1 | 5/2007 | Mastri et al. |
| 2007/0119900 A1 | 5/2007 | Ehrenfels et al. |
| 2007/0119901 A1 | 5/2007 | Ehrenfels et al. |
| 2007/0125826 A1 | 6/2007 | Shelton, IV |
| 2007/0125827 A1 | 6/2007 | Viola |
| 2007/0125828 A1 | 6/2007 | Rethy et al. |
| 2007/0145095 A1 | 6/2007 | Heinrich et al. |
| 2007/0145096 A1 | 6/2007 | Viola et al. |
| 2007/0152014 A1 | 7/2007 | Gillum et al. |
| 2007/0158385 A1 | 7/2007 | Hueil et al. |
| 2007/0170225 A1 | 7/2007 | Shelton, IV et al. |
| 2007/0175947 A1 | 8/2007 | Ortiz et al. |
| 2007/0175948 A1 | 8/2007 | Scirica et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175954 A1 | 8/2007 | Viola |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179528 A1 | 8/2007 | Soltz et al. |
| 2007/0187453 A1 | 8/2007 | Smith et al. |
| 2007/0187454 A1 | 8/2007 | Scirica |
| 2007/0187455 A1 | 8/2007 | Demmy et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0278277 A1 | 12/2007 | Wixey et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0048002 A1 | 2/2008 | Smith et al. |
| 2008/0061108 A1 | 3/2008 | Scirica |
| 2008/0078800 A1 | 4/2008 | Hess et al. |
| 2008/0078801 A1 | 4/2008 | Shelton et al. |
| 2008/0078802 A1 | 4/2008 | Hess et al. |

| | | | | | | |
|---|---|---|---|---|---|---|
| 2008/0078803 A1 | 4/2008 | Shelton et al. | | 2009/0209946 A1 | 8/2009 | Swayze et al. |
| 2008/0078804 A1 | 4/2008 | Shelton et al. | | 2009/0209990 A1 | 8/2009 | Yates et al. |
| 2008/0078805 A1 | 4/2008 | Omaits et al. | | 2009/0218384 A1 | 9/2009 | Aranyi |
| 2008/0078806 A1 | 4/2008 | Omaits et al. | | 2009/0236393 A1 | 9/2009 | Viola |
| 2008/0078807 A1 | 4/2008 | Hess et al. | | 2009/0236395 A1 | 9/2009 | Scirica |
| 2008/0078808 A1 | 4/2008 | Hess et al. | | 2009/0242610 A1 | 10/2009 | Shelton, IV et al. |
| 2008/0083806 A1 | 4/2008 | Scirica | | 2009/0242611 A1 | 10/2009 | Hathaway et al. |
| 2008/0083813 A1 | 4/2008 | Zemlok et al. | | 2009/0255974 A1 | 10/2009 | Viola |
| 2008/0110958 A1 | 5/2008 | McKenna et al. | | 2009/0255975 A1 | 10/2009 | Zemlok |
| 2008/0110961 A1 | 5/2008 | Voegele et al. | | 2009/0255976 A1 | 10/2009 | Marczyk et al. |
| 2008/0125812 A1 | 5/2008 | Zubik et al. | | 2009/0255977 A1 | 10/2009 | Zemlok |
| 2008/0149685 A1 | 6/2008 | Smith et al. | | 2009/0261142 A1 | 10/2009 | Milliman et al. |
| 2008/0164296 A1 | 7/2008 | Shelton et al. | | 2009/0261144 A1 | 10/2009 | Sniffen et al. |
| 2008/0169327 A1 | 7/2008 | Shelton et al. | | 2009/0261145 A1 | 10/2009 | Heinrich et al. |
| 2008/0169328 A1 | 7/2008 | Shelton | | 2009/0266868 A1 | 10/2009 | Wenchell et al. |
| 2008/0169329 A1 | 7/2008 | Shelton et al. | | 2009/0272784 A1 | 11/2009 | Farascioni |
| 2008/0169330 A1 | 7/2008 | Shelton et al. | | 2009/0272787 A1 | 11/2009 | Scirica |
| 2008/0169331 A1 | 7/2008 | Shelton et al. | | 2009/0277946 A1 | 11/2009 | Marczyk |
| 2008/0169332 A1 | 7/2008 | Shelton et al. | | 2009/0277947 A1 | 11/2009 | Viola |
| 2008/0169333 A1 | 7/2008 | Shelton et al. | | 2009/0277949 A1 | 11/2009 | Viola et al. |
| 2008/0210738 A1 | 9/2008 | Shelton et al. | | 2009/0283568 A1 | 11/2009 | Racenet et al. |
| 2008/0237296 A1 | 10/2008 | Boudreaux et al. | | 2009/0289096 A1 | 11/2009 | Shelton, IV et al. |
| 2008/0237298 A1 | 10/2008 | Schall et al. | | 2009/0302090 A1 | 12/2009 | Shah |
| 2008/0251568 A1* | 10/2008 | Zemlok et al. ............ 227/175.1 | | 2009/0302091 A1 | 12/2009 | Shah |
| 2008/0255607 A1* | 10/2008 | Zemlok ........................ 606/205 | | 2009/0306708 A1 | 12/2009 | Shah |
| 2008/0277447 A1 | 11/2008 | Smith et al. | | 2009/0308907 A1 | 12/2009 | Nalagatla et al. |
| 2008/0283570 A1 | 11/2008 | Boyden et al. | | 2009/0308908 A1 | 12/2009 | Green et al. |
| 2008/0283571 A1 | 11/2008 | Boyden et al. | | 2009/0308909 A1 | 12/2009 | Nalagatla et al. |
| 2008/0283572 A1 | 11/2008 | Boyden et al. | | 2009/0314820 A1 | 12/2009 | Green et al. |
| 2008/0283574 A1 | 11/2008 | Boyden et al. | | 2009/0314821 A1 | 12/2009 | Racenet |
| 2008/0283576 A1 | 11/2008 | Boyden et al. | | 2010/0001036 A1 | 1/2010 | Marczyk et al. |
| 2008/0283577 A1 | 11/2008 | Boyden et al. | | 2010/0006620 A1 | 1/2010 | Sorrentino et al. |
| 2008/0287987 A1 | 11/2008 | Boyden et al. | | 2010/0012702 A1 | 1/2010 | Marczyk |
| 2008/0296343 A1 | 12/2008 | Schall et al. | | 2010/0012703 A1 | 1/2010 | Calabrese et al. |
| 2008/0296344 A1 | 12/2008 | Cropper et al. | | 2010/0012704 A1 | 1/2010 | Racenet et al. |
| 2008/0296345 A1 | 12/2008 | Shelton, IV et al. | | 2010/0025452 A1 | 2/2010 | Whitman |
| 2008/0296346 A1 | 12/2008 | Shelton, IV et al. | | 2010/0032470 A1 | 2/2010 | Hess et al. |
| 2008/0296347 A1 | 12/2008 | Shelton, IV et al. | | 2010/0044411 A1 | 2/2010 | Viola |
| 2008/0302854 A1 | 12/2008 | Rethy et al. | | 2010/0065605 A1 | 3/2010 | Shelton et al. |
| 2008/0308601 A1 | 12/2008 | Timm et al. | | 2010/0065606 A1 | 3/2010 | Stopek et al. |
| 2008/0308602 A1 | 12/2008 | Timm et al. | | 2010/0065608 A1 | 3/2010 | Olson et al. |
| 2008/0308603 A1 | 12/2008 | Shelton, IV et al. | | 2010/0069942 A1 | 3/2010 | Shelton, IV et al. |
| 2008/0308604 A1 | 12/2008 | Timm et al. | | 2010/0072251 A1 | 3/2010 | Baxter, III et al. |
| 2008/0308606 A1 | 12/2008 | Timm et al. | | 2010/0072252 A1 | 3/2010 | Baxter, III et al. |
| 2008/0308607 A1 | 12/2008 | Timm et al. | | 2010/0072253 A1 | 3/2010 | Baxter, III et al. |
| 2008/0314954 A1 | 12/2008 | Boudreaux | | 2010/0072254 A1 | 3/2010 | Aranyi et al. |
| 2008/0314955 A1 | 12/2008 | Boudreaux et al. | | 2010/0072255 A1 | 3/2010 | Olson et al. |
| 2008/0314957 A1 | 12/2008 | Boudreaux | | 2010/0072256 A1 | 3/2010 | Baxter, III et al. |
| 2008/0314961 A1 | 12/2008 | Boudreaux et al. | | 2010/0072258 A1 | 3/2010 | Farascioni et al. |
| 2008/0314962 A1 | 12/2008 | Boudreaux | | 2010/0076429 A1 | 3/2010 | Heinrich |
| 2009/0001121 A1 | 1/2009 | Hess et al. | | 2010/0076459 A1 | 3/2010 | Farascioni |
| 2009/0001123 A1 | 1/2009 | Morgan et al. | | 2010/0211053 A1* | 8/2010 | Ross et al. ........................ 606/1 |
| 2009/0001124 A1 | 1/2009 | Hess et al. | | 2011/0017801 A1* | 1/2011 | Zemlok et al. ............ 227/175.1 |
| 2009/0001125 A1 | 1/2009 | Hess et al. | | 2011/0022032 A1* | 1/2011 | Zemlok et al. .................... 606/1 |
| 2009/0001126 A1 | 1/2009 | Hess et al. | | 2011/0278343 A1* | 11/2011 | Knodel et al. ............ 227/176.1 |
| 2009/0001130 A1 | 1/2009 | Hess et al. | | | | |
| 2009/0005808 A1 | 1/2009 | Hess et al. | | | | |
| 2009/0008424 A1 | 1/2009 | Green | | | | |
| 2009/0050671 A1 | 2/2009 | Racenet et al. | | | | |
| 2009/0057370 A1 | 3/2009 | Marczyk et al. | | | | |
| 2009/0065549 A1 | 3/2009 | Viola | | | | |
| 2009/0065550 A1 | 3/2009 | Green et al. | | | | |
| 2009/0065551 A1 | 3/2009 | Green et al. | | | | |
| 2009/0078738 A1 | 3/2009 | Racenet et al. | | | | |
| 2009/0078739 A1 | 3/2009 | Viola | | | | |
| 2009/0084826 A1 | 4/2009 | Shah et al. | | | | |
| 2009/0090763 A1 | 4/2009 | Zemlok et al. | | | | |
| 2009/0090764 A1 | 4/2009 | Viola | | | | |
| 2009/0090765 A1 | 4/2009 | Blier et al. | | | | |
| 2009/0090766 A1 | 4/2009 | Knodel | | | | |
| 2009/0095790 A1 | 4/2009 | Whitman et al. | | | | |
| 2009/0101692 A1 | 4/2009 | Whitman et al. | | | | |
| 2009/0101694 A1 | 4/2009 | Marczyk | | | | |
| 2009/0105535 A1 | 4/2009 | Green | | | | |
| 2009/0108048 A1 | 4/2009 | Zemlok et al. | | | | |
| 2009/0108049 A1 | 4/2009 | Roy | | | | |
| 2009/0114699 A1 | 5/2009 | Viola | | | | |
| 2009/0114700 A1 | 5/2009 | Marczyk | | | | |
| 2009/0114701 A1 | 5/2009 | Zemlok et al. | | | | |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |

| | | | | | | |
|---|---|---|---|---|---|---|
| EP | 0484677 | 5/1992 | | EP | 1987782 A2 | 11/2008 |
| EP | 0489436 | 6/1992 | | EP | 2005900 A2 | 12/2008 |
| EP | 0503662 | 9/1992 | | FR | 2542188 | 9/1984 |
| EP | 0514139 | 11/1992 | | FR | 2660851 | 10/1991 |
| EP | 0536903 | 4/1993 | | FR | 2681775 | 10/1991 |
| EP | 0537572 | 4/1993 | | GB | 1352554 | 4/1971 |
| EP | 0539762 | 5/1993 | | GB | 1452185 | 10/1976 |
| EP | 0545029 | 6/1993 | | GB | 1555455 | 11/1979 |
| EP | 0552050 | 7/1993 | | GB | 2048685 | 12/1980 |
| EP | 0552423 | 7/1993 | | GB | 2070499 | 9/1981 |
| EP | 0579038 | 1/1994 | | GB | 2141066 | 12/1984 |
| EP | 0589306 | 3/1994 | | GB | 2165559 | 4/1986 |
| EP | 0591946 | 4/1994 | | SU | 659146 | 4/1979 |
| EP | 0592243 | 4/1994 | | SU | 728848 | 5/1980 |
| EP | 0593920 | 4/1994 | | SU | 980703 | 12/1982 |
| EP | 0598202 | 5/1994 | | SU | 990220 | 1/1983 |
| EP | 0598579 | 5/1994 | | WO | WO8302247 | 7/1983 |
| EP | 0621006 | 10/1994 | | WO | WO 89/10094 | 11/1989 |
| EP | 0621009 | 10/1994 | | WO | WO9210976 | 7/1992 |
| EP | 0656188 | 6/1995 | | WO | 9308754 | 5/1993 |
| EP | 0365153 | 8/1995 | | WO | 9314706 | 8/1993 |
| EP | 0666057 | 8/1995 | | WO | WO 03/026511 | 4/2003 |
| EP | 0705571 | 4/1996 | | | | |
| EP | 0760230 | 3/1997 | | | | |
| EP | 1 769 754 | 4/2007 | | | | |
| EP | 1964524 A1 | 9/2008 | | | | |
| EP | 1980214 A2 | 10/2008 | | | | |

OTHER PUBLICATIONS

European Search Report dated Jul. 28, 2011 for EP 11 15 2266.

* cited by examiner

ONE HANDED STAPLER

CROSS REFERENCE TO RELATED APPLICATION

The present application claims the benefit of and priority to U.S. Provisional Application Ser. No. 61/234,369 filed on Aug. 17, 2009, the entire contents of which are incorporated herein by reference.

BACKGROUND

1. Technical Field

The present disclosure relates to a surgical stapling device and, more particularly, to an endoscopic surgical stapling device having a tool assembly and an endoscopic body portion, wherein the anvil is pivoted by a motor and the staples are fired manually.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars or cam wedge that travel longitudinally through the staple cartridge, with the cam bars or cam wedge acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. Nos. 3,079,606 and 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam to effect ejection of the staples from the staple cartridge of the disposable loading unit. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.). U.S. Surgical, the assignee of the present application, has manufactured and marketed endoscopic stapling instruments, such as the Multifire ENDO GIA* 30 and Multifire ENDO GIA* 60 instruments, for several years. These instruments have provided significant clinical benefits. Nonetheless, improvements are possible.

SUMMARY

In accordance with the present disclosure, a surgical instrument is provided. The surgical instrument has a handle assembly and an elongate body extending distally from the handle assembly. The handle assembly includes a handle and a switch. The switch allows the handle to have multiple modes of operation. At least one of the modes of operation is a firing mode, a clamping mode, or a retraction mode. The switch extends through both the left and right hand sides of the handle assembly.

The elongate body has a distal portion and defines a longitudinal axis. A first jaw member is supported by the elongate body and contains a plurality of fasteners. A second jaw member is mounted adjacent the first jaw member and is movable in relation to the first jaw member between an open position and a closed position by the handle assembly. The handle assembly is also connected to an actuation member and able to move the actuation member relative to the first jaw member to sequentially eject fasteners.

The switch is configured to move a slider cam over a rack member located within the handle assembly. The rack member has two sets of teeth that are diametrically opposed. A first set of teeth points distally along the longitudinal axis and is configured to engage a first pawl. A second set of teeth points proximally along the longitudinal axis and is configured to engage a second pawl. The first pawl pivots about a distal region of the first pawl. The second pawl pivots about a proximal region of the second pawl.

The surgical instrument has an articulation mechanism that pivots the distal portion of the elongate body about the longitudinal axis. The articulation mechanism includes a motor and power supply.

BRIEF DESCRIPTION OF THE DRAWINGS

The accompanying drawings, which are incorporated in and constitute a part of this specification, illustrate embodiments of the disclosure, and together with a general description of the disclosure given above, and the detailed description of the embodiments given below, serve to explain the principles of the disclosure.

Figure 1:
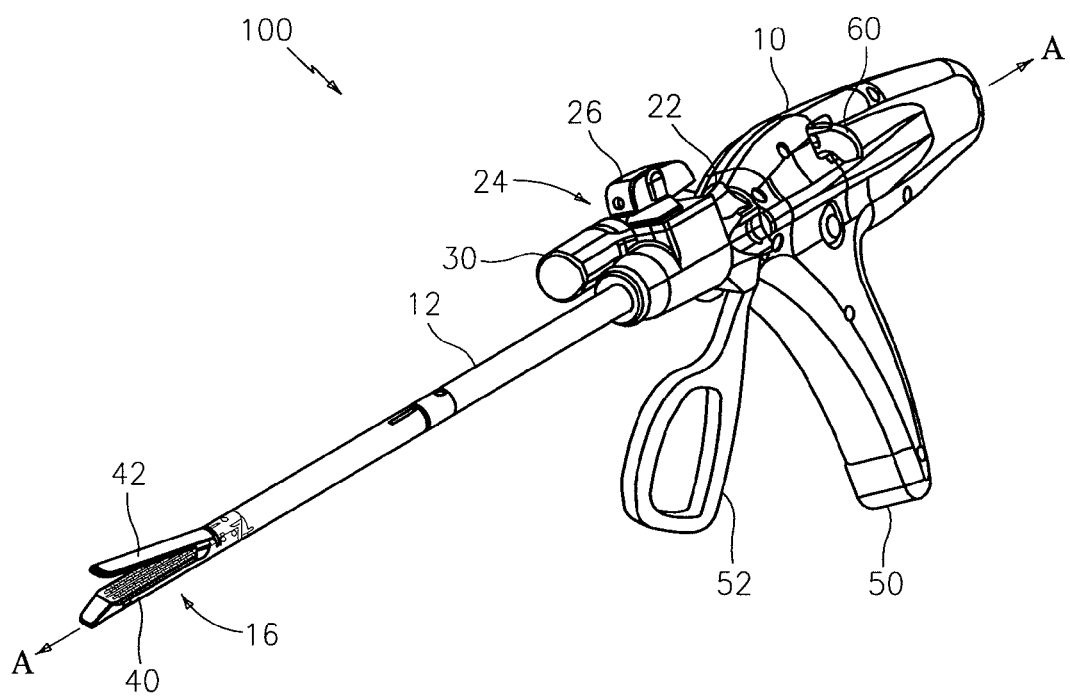
FIG. 1 is a perspective view of the surgical instrument in accordance with the principles of the present disclosure.

Other features and advantages of the present disclosure will become apparent from the following detailed description, taken in conjunction with the accompanying drawings, which illustrate, by way of example, the principles of the present disclosure.

DETAILED DESCRIPTION

In the drawings and in the description which follows, the term "proximal", as is traditional, will refer to the end of the apparatus which is closest to the operator, while the term "distal" will refer to the end of the apparatus which is furthest from the operator.

The present disclosure can be used with any fastening device known in the art and is intended to encompass the same, shall be discussed in terms of both conventional and endoscopic procedures and apparatus. However, the use herein of terms such as "endoscopic", "endoscopically", and "endoscopic portion", among others, should not be construed to limit the present disclosure to an apparatus for use only in conjunction with an endoscopic tube. The apparatus of present disclosure may find use in procedures in these and other uses including but not limited to where access is limited to a small incision such as in arthroscopic and laparoscopic procedures, or other conventional medical procedures (i.e. Open procedures).

Figure 2:
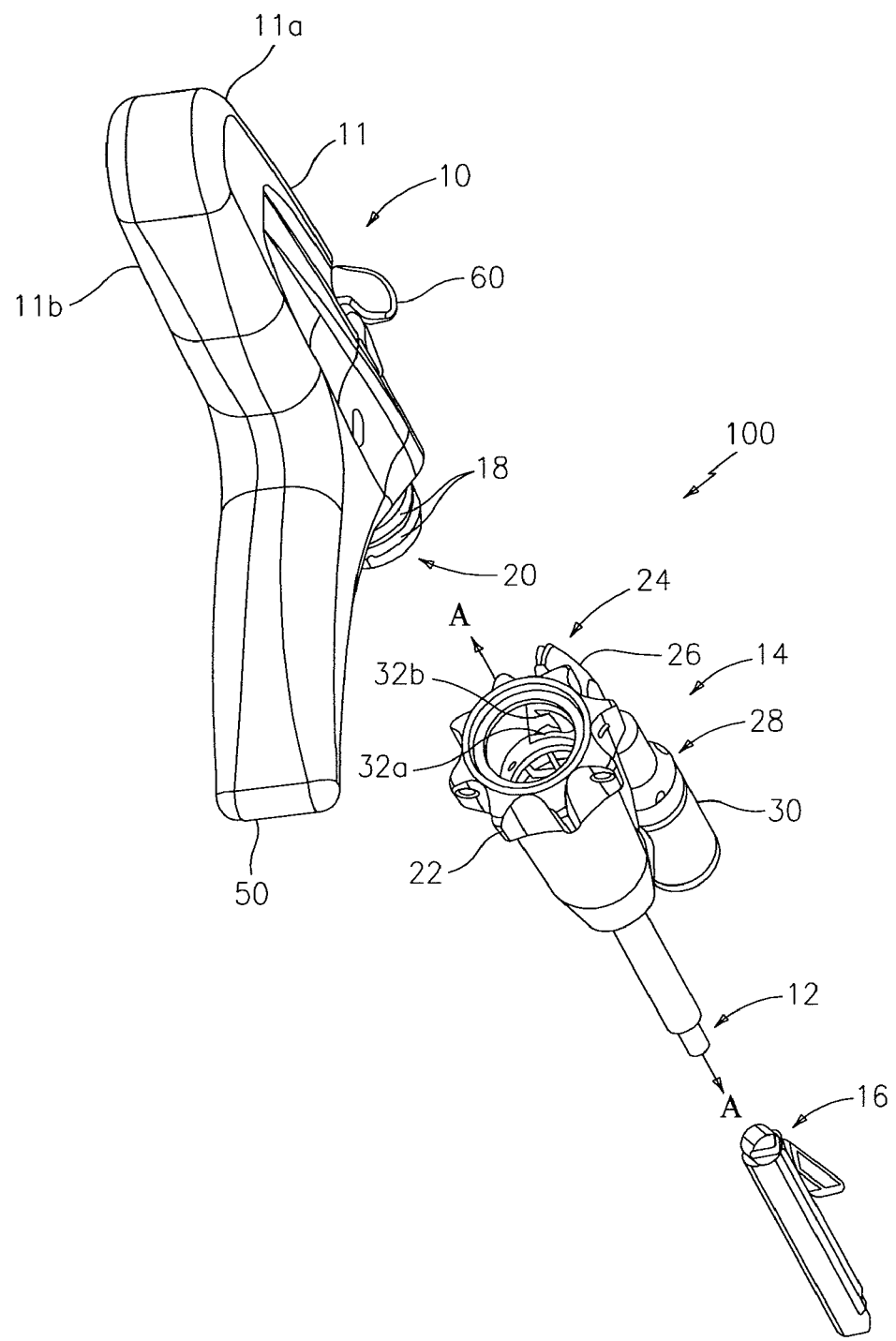
FIG. 2 is a perspective view of the surgical instrument of FIG. 1, with parts separated.

Now referring to FIGS. 1 and 2, a surgical instrument, e.g., a surgical stapler, in accordance with embodiments of the present disclosure is referred to as reference numeral 100. Surgical instrument 100 includes a handle assembly 10, an endoscopic portion 12 and an end effector 16 defining a longitudinal axis A-A extending therethrough. Further details of surgical instrument 100 are included in U.S. patent application Ser. No. 11/544,061, filed on Oct. 6, 2006, the entire contents of which are hereby incorporated by reference herein. While the features of the embodiments illustrated in FIG. 1 is shown in connection with a particular type of surgical instrument 100, it is envisioned that the features described with respect to FIG. 1 are operable with other surgical instruments.

With continued reference to FIGS. 1 and 2, endoscopic portion 12 extends distally from handle assembly 10. End effector 16 is selectively connectable to a distal end of endoscopic portion 12. The endoscopic portion 12 is rotatable about axis A-A relative to distal portion 20 of handle assembly 10. A knob 22 is shown in mechanical cooperation with endoscopic portion 14 to facilitate such rotation.

Handle assembly 10 includes a stationary handle 50, a moveable handle 52, and electrical contacts (i.e., conductive rings 18) disposed adjacent distal portion 20 of the handle assembly 10. Conductive rings 18 are internally wired within handle assembly 10 to a power source (either within handle assembly 10 or external thereto) and/or a micro controller. It is envisioned that conductive rings 18 are removable from handle assembly 10.

Endoscopic portion 12 is shown having an articulation mechanism or actuator 24 disposed in mechanical cooperation therewith. As discussed above, articulation mechanism 24 is configured to pivot end effector 16 with respect to a longitudinal axis "A-A". Here, an articulation knob 26 that is operatively disposed on endoscopic portion 12, and a motor 28 disposed within a housing 30 of endoscopic portion 12 may be used to articulate end effector 16 engaged with endoscopic portion 12.

The motor 28 is used to provide articulation and has at least one electrical contact 32 (a pair of electrical contacts 32a and 32b is shown) operably disposed with endoscopic portion 12. Electrical contact 32 is in electrical communication with motor 28 of endoscopic portion 12 and is configured to communicate electrical power between conductive rings 18 of handle assembly 10 and motor 28. Here, motor 28 is operatively connected to the actuation member to move the actuation member substantially along longitudinal axis A-A, i.e. to articulate end effector 16. It is envisioned that motor 28 provides or helps provide power that is helpful for articulation of end effector 16, rotation of endoscopic portion 12, etc.

Conductive rings 18 are substantially circular in shape and disposed around distal portion 20 of handle assembly 10. As can be appreciated, the shape and/or configuration of conductive rings 18 around distal portion 20 of handle assembly 10 helps allow substantially continuous contact between conductive rings 18 and electrical contacts 32 as endoscopic portion 12 is being rotated about longitudinal axis A-A with respect to handle assembly 10. Thus, a complete 360° rotation is possible. Further, communication of power between motor 28 and electrical contact 32 is possible notwithstanding the rotational direction of endoscopic portion 12 with respect to handle assembly 10. Additionally, it is envisioned that mechanical and/or electrical stops may be disposed on endoscopic portion 12 and/or distal portion 20 of handle assembly 10 to limit rotational displacement of endoscopic portion 12.

While only one type of end effector 16 is illustrated in FIG. 1, it is contemplated that several types of end effectors 16 (e.g., a pivotable cartridge assembly, end effectors including a substantially circular cartridge assembly, parallel approximating jaw members, configured for sequential firing of staples and/or configured for simultaneous firing of staples) may be used in connection with surgical instrument 100 and may be usable with different types of endoscopic portions 12.

Figure 3:
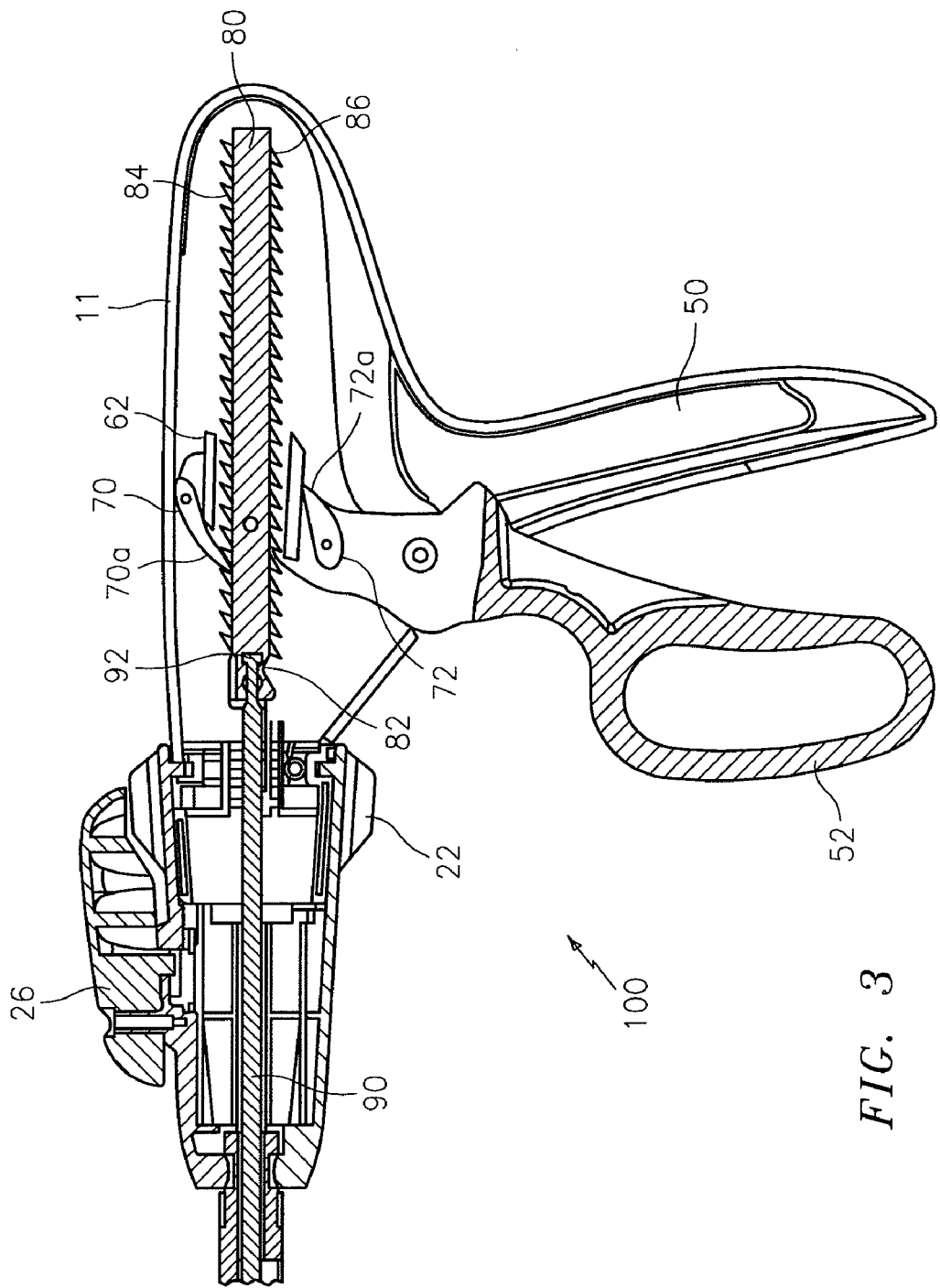
FIG. 3 is a side cross-sectional view of the surgical instrument of FIG. 1.

Referring additionally to FIG. 3, the end effector 16 includes a cartridge assembly 40 and an anvil assembly 42. Cartridge assembly 40 and anvil assembly 42 further define a pair of jaws. Cartridge assembly 40 houses a plurality of staples and a drive mechanism (not shown). An example of a drive mechanism is disclosed in U.S. patent application Ser. No. 10/700,250, filed on Nov. 3, 2003, the entire contents of which are hereby incorporated by reference. Anvil assembly 42 is movable in relation to cartridge assembly 40 between an open position spaced from cartridge assembly 40 and an approximated or clamped position in juxtaposed alignment with cartridge assembly 40. End effector 16 may alternatively be arranged such that cartridge assembly 40 is movable in relation to anvil assembly 42. Drive mechanism (not shown) is configured to eject the plurality of staples from the cartridge assembly 40 upon actuation from a drive rod 80. The drive rod 90 is coupled through an actuation shaft 80 to the movable handle 52.

Switch 60 (FIG. 1) is configured to alternate the function of movable handle 52 between a grasping or "firing" mode and a "return" mode. In firing mode, end effector 16 is configured to operate as a grasping jaw mechanism, i.e., anvil assembly 42 is movable in relation to cartridge assembly 40 to grasp tissue therebetween and apply the fasteners therethrough. In return mode, end effector 16 is configured to operate as a releasing mechanism, i.e., anvil assembly 42 is movable in relation to cartridge assembly 40 to release the tissue.

Switch 60 includes a slide cam 62. Switch 60 is configured to be engaged by the surgeon's finger to move slide cam 62 along an actuation shaft 80 within the handle assembly. As to be appreciated, alternatives to switch 60 are also contemplated, e.g., knobs, levers, depressible buttons, toggles, trigger assemblies, etc.

Handle assembly 10 includes a housing 11 formed from a pair of molded half-sections 11a and 11b (FIG. 2), which forms stationary handle 50. Half-sections 11a and 11b are formed of a thermoplastic material, e.g., polycarbonate. Alternately, other materials having the requisite strength requirements may be used to form housing 11, e.g., surgical grade metals. Housing 11 half-sections 11a and 11b are secured to each other using known fastening techniques, e.g., adhesives, welding, interlocking structure, screws, etc. Alternately, other fastening techniques may be used.

Referring to FIG. 1, movable handle 52 is rotatably supported between housing half-sections 11a and 11b. A biasing member (not shown), e.g., a torsion spring, may be included to urge movable handle 52 away from stationary handle 50 to a non-compressed position. An advancement pawl 70, as shown in FIG. 3, is rotatably supported on movable handle 50 and is biased by a spring (not shown) towards the actuation shaft 80. A return pawl 72 is also rotatably supported on movable handle 50 and is biased by a spring (not shown) towards the actuation shaft 80.

Actuation shaft 80 is slidably supported between retracted and advanced positions within housing 11 and includes a distal end defining a recess 82 configured to rotatably receive the proximal end 92 of a drive rod 90. Actuation shaft 80 includes a first toothed rack 84 and a second toothed rack 86. Advancement pawl 70 has an engagement finger 70a, which is biased by spring (not shown) towards toothed rack 84 of actuation shaft 80. Return pawl 72 has an engagement finger 72a, which is biased by spring (not shown) towards second toothed rack 86 of actuation shaft 80.

Slide cam 62 is placed about actuation shaft 80 and is movable from a firing position and a return position by movement of switch 60. In the firing position, the slide cam 62 is moved between the engagement finger 72a of return pawl 72 and the second toothed rack 86. When movable handle 52 is actuated while slide cam 62 is in a firing position, i.e., is pivoted towards stationary handle 50 against the bias of a torsion spring (not shown), engagement finger 70a of advancement pawl 70 engages the first toothed rack 84 of actuation shaft 80 to advance actuation shaft 80 and drive rod 90 distally. As the drive rod 90 is advanced, the anvil assembly 42 moves toward the cartridge assembly 40 until the tissue therebetween is compressed and the drive mechanism 44 ejects the fasteners from the cartridge assembly 40.

In the return position, the slide cam 62 is moved between the engagement finger 70a of advancement pawl 70 and the first toothed rack 84. When movable handle 52 is actuated while slide cam 62 is in a return position, i.e., is pivoted towards stationary handle 50 against the bias of a torsion spring (not shown), engagement finger 72a of return pawl 72 engages the second toothed rack 86 of actuation shaft 80 to retract actuation shaft 80 and drive rod 90 proximally. As the drive rod 90 is retracted, the anvil assembly 42 moves away from the cartridge assembly 40 releasing the tissue.

Figure 4:
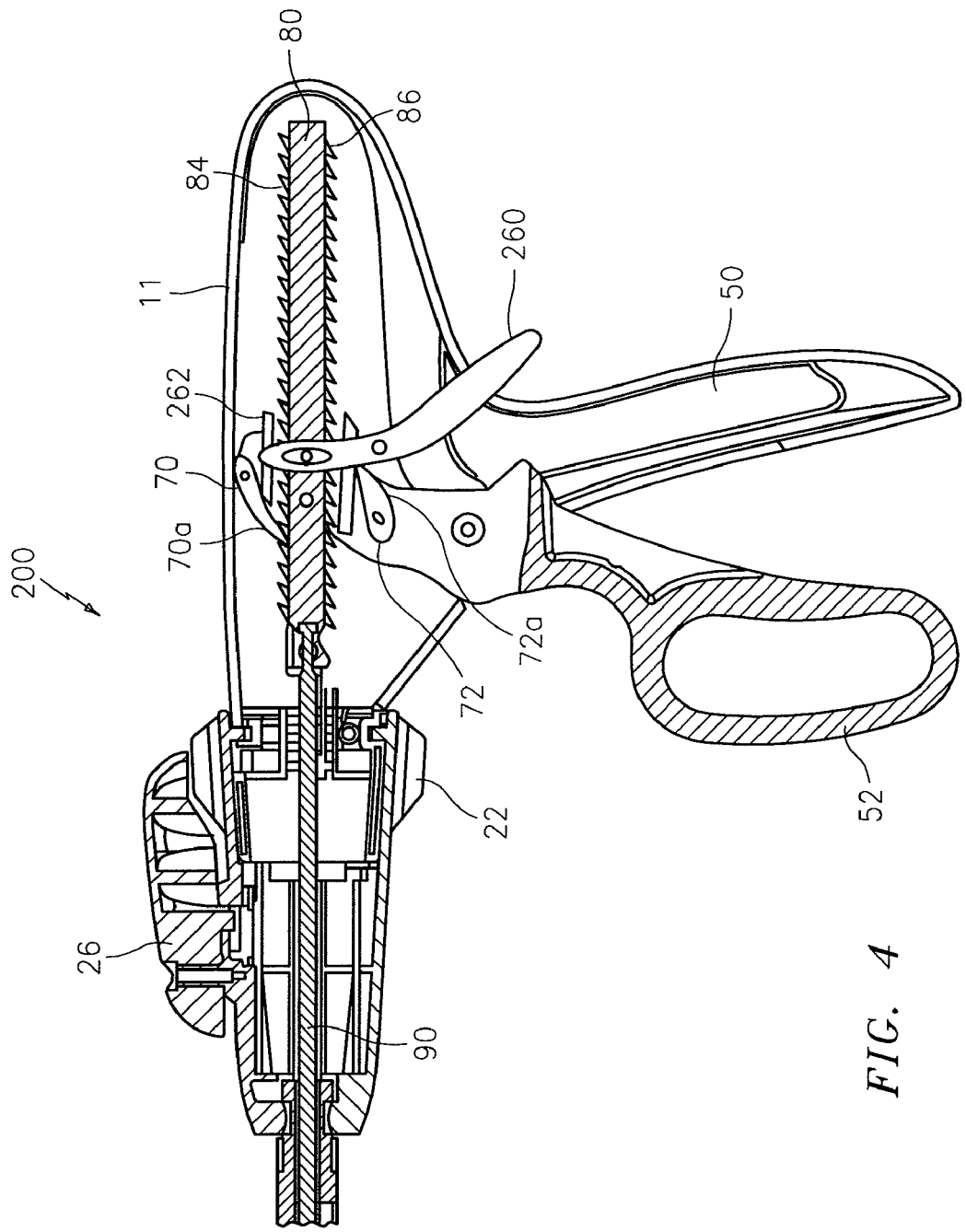
FIG. 4 is a side cross-sectional view of another embodiment of a surgical instrument.

Now referring to FIG. 4, another embodiment of surgical instrument 200 includes a slide cam 262 connected to a lever 260. Lever 260 acts similarly to switch 60 above to move the slide cam 262 from a firing position to a return position.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended hereto.

Although being shown as an endoscopic surgical stapler, the present system may be used with any fastener applier known in the art.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed:

1. A surgical instrument comprising:
    a handle assembly including a handle;
    an elongate body extending distally from the handle assembly and defining a longitudinal axis, the elongate body having a distal portion;
    a first jaw member supported by the elongate body and containing a plurality of fasteners;
    an second jaw member mounted adjacent the first jaw member, the second jaw member being configured to move in relation to the first jaw member between an open position and a closed position upon actuation of the handle assembly; and
    a switch operatively connected to the handle assembly, the switch being configured to alternate the handle assembly between at least two modes of operation, wherein the switch extends through two sides of the handle assembly.

2. The surgical instrument of claim 1, wherein the modes of operation include at least one selected from a group consisting of a firing mode, a clamping mode, and a retraction mode.

3. The surgical instrument of claim 1, further comprising an actuation member, wherein the handle assembly is operably connected to the actuation member and is configured to move the actuation member relative to the first jaw member to effectuate sequential ejection of the fasteners through an actuation stroke.

4. The surgical instrument of claim 1, wherein the handle assembly includes a first and second pawl, the first pawl being pivotable about a proximal section and the second pawl being pivotable about a distal section.

5. The surgical instrument of claim 1, wherein the handle assembly includes a rack member having a first and a second set of teeth arranged or disposed in a diametrically opposed relation.

6. The surgical instrument of claim 1, further comprising an articulation mechanism configured to pivot the distal portion of the elongate body about the longitudinal axis.

7. The surgical instrument of claim 6, wherein the articulation mechanism includes a motor.

8. The surgical instrument of claim 6, further comprising a power supply.

9. A surgical instrument comprising:
    a handle assembly including a handle;
    an elongate body extending distally from the handle assembly and defining a longitudinal axis, the elongate body having a distal portion;
    a first jaw member supported by the elongate body and containing a plurality of fasteners;
    an second jaw member mounted adjacent the first jaw member, the second jaw member being configured to move in relation to the first jaw member between an open position and a closed position upon actuation of the handle assembly; and
    a switch operatively connected to the handle assembly, the switch being configured to alternate the handle assembly between at least two modes of operation, wherein the switch is adapted to move a slider cam.

10. The surgical instrument of claim 9, wherein the modes of operation include at least one selected from a group consisting of a firing mode, a clamping mode, and a retraction mode.

11. The surgical instrument of claim 9, further comprising an actuation member, wherein the handle assembly is operably connected to the actuation member and is configured to move the actuation member relative to the first jaw member to effectuate sequential ejection of the fasteners through an actuation stroke.

12. The surgical instrument of claim 9, wherein the handle assembly includes a first and second pawl, the first pawl being pivotable about a proximal section and the second pawl being pivotable about a distal section.

13. The surgical instrument of claim 9, wherein the handle assembly includes a rack member having a first and a second set of teeth arranged or disposed in a diametrically opposed relation.

14. The surgical instrument of claim 9, further comprising an articulation mechanism configured to pivot the distal portion of the elongate body about the longitudinal axis.

15. The surgical instrument of claim 14, wherein the articulation mechanism includes a motor.

16. The surgical instrument of claim 14, further comprising a power supply.

17. The surgical instrument of claim 9, wherein the slider cam is movable between a firing position and a return position.

18. The surgical instrument of claim 17, wherein in the firing position, the slider cam is disposed between an engagement finger of a return pawl and a toothed rack and wherein in the return position, the slider cam is disposed between an engagement finger of an advancement pawl and another toothed rack.

* * * * *